(12) United States Patent
Chen et al.

(10) Patent No.: US 7,397,042 B2
(45) Date of Patent: Jul. 8, 2008

(54) OPTICAL DETECTION APPARATUS AND METHOD THEREOF

(75) Inventors: Chien-An Chen, Hsinchu (TW); Han-Wei Wang, Taichung (TW); Chi-Fu Hung, Nantou County (TW)

(73) Assignee: DR. Chip Biotechnology Incorporation, Chu-Nan, Miao-Li County (TW)

( * ) Notice: Subject to any disclaimer, the term of this patent is extended or adjusted under 35 U.S.C. 154(b) by 119 days.

(21) Appl. No.: 11/209,685

(22) Filed: Aug. 24, 2005

(65) Prior Publication Data

US 2007/0051903 A1    Mar. 8, 2007

(51) Int. Cl.
*G21K 5/00* (2006.01)
(52) U.S. Cl. .................................................. 250/458.1
(58) Field of Classification Search ................ 250/458.1
See application file for complete search history.

(56) References Cited

U.S. PATENT DOCUMENTS

| | | | |
|---|---|---|---|
| 5,719,391 A | | 2/1998 | Kain |
| 5,760,416 A * | | 6/1998 | Tsuchiya, deceased ..... 250/584 |
| 5,780,857 A | | 7/1998 | Harju et al. |
| 5,796,112 A * | | 8/1998 | Ichie ........................ 250/458.1 |
| 5,981,956 A * | | 11/1999 | Stern ........................ 250/458.1 |
| 6,049,351 A * | | 4/2000 | Noguchi et al. ............. 347/249 |
| 6,355,934 B1 | | 3/2002 | Osgood et al. |
| 6,471,916 B1 | | 10/2002 | Noblett |
| 6,603,537 B1 | | 8/2003 | Dietz et al. |
| 6,628,385 B1 | | 9/2003 | Osipchuk et al. |
| 6,630,063 B1 | | 10/2003 | Li et al. |
| 6,646,271 B2 | | 11/2003 | Yokokawa et al. |
| 6,664,537 B2 | | 12/2003 | Engelhardt et al. |
| 6,819,468 B2 | | 11/2004 | Dho |
| 2006/0102851 A1* | | 5/2006 | Jalink et al. .............. 250/461.2 |

* cited by examiner

*Primary Examiner*—David P. Porta
*Assistant Examiner*—Marcus H Taningco
(74) *Attorney, Agent, or Firm*—Birch, Stewart, Kolasch & Birch, LLP

(57) ABSTRACT

An optical detection apparatus and method thereof is provided, which is applicable for detecting the image signals of a labeled sample. First, a laser module provides excitation light, and the excitation light is continuously reflected by a scan module for providing linear scanning light by changing a reflection angle. The carrier moves the light module in a direction nonparallel to the linear direction so as to provide a two-dimensional testing zone. The labeled sample placed in the testing zone is excited by the linear scanning light and generates emission light to be received by the light receiver. Therefore, the light receiver forms the image signals of the labeled sample corresponding to the emission light.

16 Claims, 7 Drawing Sheets

OPTICAL DETECTION APPARATUS AND METHOD THEREOF

BACKGROUND

1. Field of the Invention

The invention relates to an apparatus and method for detecting optical signals, and particularly to an apparatus and method for detecting two-dimension optical image signals.

2. Description of the Related Art

FIG. 1 shows a systematic view of a general apparatus for fluorescence signals detection. A sampling light beam L1' passes an excitation filter or a monochromator 110. The filter or monochromator 110 lets the excitation laser L1 pass through and irradiate the labeled sample 120 in the testing zone. The labeled sample 120 is excited to radiate fluorescence. The emission light L2 passes a second filter or a monochromator 112 where unneeded noise light is removed. Then, a monochromical emission is detected by a photodetector 130.

There are two technical manners for detecting fluorescence signals. The first manner is to apply laser as an excitation light and apply a photomultiplier tube (PMT) to detect the received signal and form a two-dimensional image. The second manner is to apply white light of mercury lamp or xenon lamp and to use a high-resolution camera, such as a CCD (charge-coupled device) camera, to take the fluorescence picture for further image analysis through an image analyzer.

The laser and photomultiplier tube detection system mainly follows the structure of an optical microscope. As shown in FIG. 2, a laser source 202 provides a laser beam to be separated by a dichroic mirror 210 and focused in the testing zone. The labeled sample 220 in the testing zone is excited to radiate fluorescence. The dichroic mirror 210 separates the excitation laser and the emission light into different paths. The light source is focused by lens into a spot. The size of the spot determines the resolution of the detection system. However, the size of the spot is restricted by the optical limitation of diffraction and the wavelength of the incident light. Furthermore, since the detection signal is processed with pixel of the focused spot, a precise moving device with displacement resolution higher than the optical resolution is required for obtaining a two-dimensional scanning. The precise device increases the hardware cost. The single point scanning also increases the imaging time and slows the operation.

There have been many prior devices for detecting fluorescence signals. For example, U.S. Pat. No. 5,719,391 discloses a fluorescence imaging system including an objective entrance pupil and a two-dimensional moving system. U.S. Pat. No. 5,780,857 discloses a scanning system with both laser and white light beams. U.S. Pat. Nos. 6,355,934, 6,471,916, 6,603,537, 6,628,385, 6,646,271 and 6,664,537 also disclose other derivative devices. Most of them are laser and photomultiplier tube systems using dichroic mirrors to separate the incidence excitation laser and the emission light. When omitting the dichroic mirror, the optical design may sacrifice the wholeness of entrance aperture of the received emission light.

The other detection devices with CCD cameras mainly use white light sources. However, the white light source occupies much space and generates a lot of heat that cause trouble and difficulty of system design. The system also requires two filters, in which one removes the excessive wavelength light in the incidence beam; the other removes the noise in the emission light. A dichroic mirror is also required to separate the incidence light and the emission light.

U.S. Pat. No. 6,630,063 discloses a fluorescence signal detection system applying capillary electrophoresis. The system also uses a laser beam refracted by lens and formed into scanning beams through a galvanometer. However, instead of two-dimensional scanning, it is only applicable to one-dimensional scanning.

SUMMARY

Accordingly, the present invention is directed to an optical detection apparatus and method thereof applying a one-dimensional scanning laser beam and a one-dimensional moving carrier to achieve two-dimensional fluorescence signal detection, so as to solve the problems and restrictions of prior arts.

In one aspect, the optical detection apparatus and method thereof according to the invention does not use dichroic mirror so as to simplify the optical design and save cost.

In another aspect, the optical detection apparatus and method thereof according to the invention is applicable to the field of biochips for reading the signals. The biochips include micro-array chips, micro fluidic chips, DNA chips, protein arrays, tissue arrays, Lab-on-a-chip and other kinds of glass or polymer slides.

In yet another aspect, the optical detection apparatus and method thereof according to the invention has both abilities to detect the signals for fluorescence labelling signals and the colorimetric signals.

In order to achieve the aforesaid objects, the optical detection apparatus according to the invention, applicable for detecting the image signals of a labeled sample and includes a laser module, a scan module, a carrier and a light receiver. The laser module provides excitation light and then transmits the excitation light, and the scan module continuously reflects the excitation light and then introduces the excitation light to provide a linear scanning light by changing a reflection angle. The carrier moves the scan module in a direction nonparallel to a direction of the linear scanning light so as to provide a two-dimensional testing zone. In this case, the preferred direction, in which the carrier moves, is perpendicular to the direction of the linear scanning light. The labeled sample placed in the testing zone is excited by the excitation light and generates emission light to be received by the light receiver. Therefore, the light receiver acquires the image signals of the labeled sample according to the emission light.

The scan module is as a polygonal mirror and a motor, or as a galvanometer which includes a reflective mirror and a driving unit. Moreover, the polygonal mirror includes a polyhedron rotor having poly reflective surfaces, or is formed with mirrors. The polyhedron rotor having poly reflective surfaces may be made of a polyhedron rotor and scanning mirrors embedded thereon.

Further, the laser module can be a laser generator or an array with many laser generators, such as an array of laser diodes. Moreover, the laser module further includes a collimation and coupling lenses connected to the laser generator(s). When the laser module includes a laser generator and a collimation and coupling lenses, the laser generator generates laser beam, and then the laser beam is collimated and guided by a collimation and coupling lenses. When the laser module includes many laser generators and a collimation and coupling lenses, the laser generators generate laser beams with different wavelengths, respectively; and then the laser beams are coupled into the excitation light by a collimation and coupling lenses.

Furthermore, the laser generator(s) can be carried by the carrier or steadfastly installed. When the laser generator(s)

is/are steadfastly installed, the laser module further includes a mirror, which is carried by the carrier to move with the scan module, for reflecting the excitation light from the collimation and coupling lenses to the scan module.

The emission light emitted from the labeled sample can be guided to the light receiver via at least one mirror.

The light receiver has an image-sensing module, such as a charge-coupled device (CCD). A cooling element can be applied to reduce the dark current of the CCD.

The optical detection apparatus according to the invention further includes a light generator used to illuminate the labeled sample evenly so as to help detecting the colorimetric image signals of the labeled sample.

Further, the optical detection method according to the invention comprises the following steps. First, provide linear scanning light at a tilt angle. Then, move the linear scanning light in a direction nonparallel to linear direction of the linear scanning light to form a two-dimensional testing zone. Further, illuminate and excite a labeled sample in the testing zone to emit emission light. And, receive the emission light and form image signal of the labeled sample according to the emission light. Moreover, the preferred direction, in which the linear scanning light is moved, is perpendicular to the linear direction.

In the step of providing the linear scanning light at a tilt angle, there are steps of generating excitation light, and continuously reflecting the excitation light with change of the reflection angle to form the linear scanning line.

The optical detection method according to the invention further comprises a step of guiding the emission light via at least a mirror into a receiving portion according to the emission light. In other words, the testing zone, the mirror and the light receiver are serially arranged in an emission light path.

BRIEF DESCRIPTION OF THE DRAWINGS

The invention will become more fully understood from the detailed description given herein below. However, this description is for purposes of illustration only, and thus is not limitative of the invention, wherein.

DETAILED DESCRIPTION OF THE INVENTION

Figure 1:
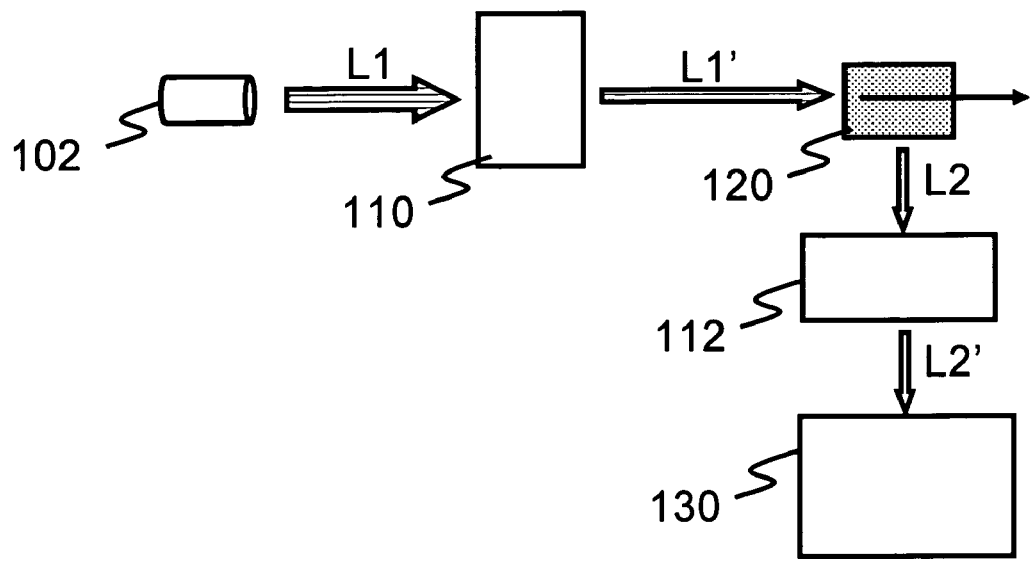
FIG. 1 is a systematic view of a conventional fluorescence detection apparatus.
Figure 2:
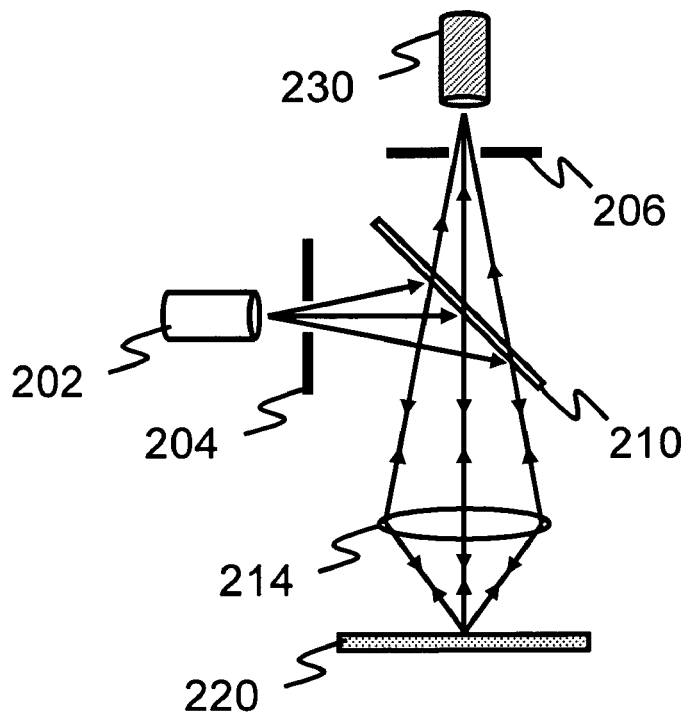
FIG. 2 is a constructional view of another conventional fluorescence detection apparatus.
Figure 3A:
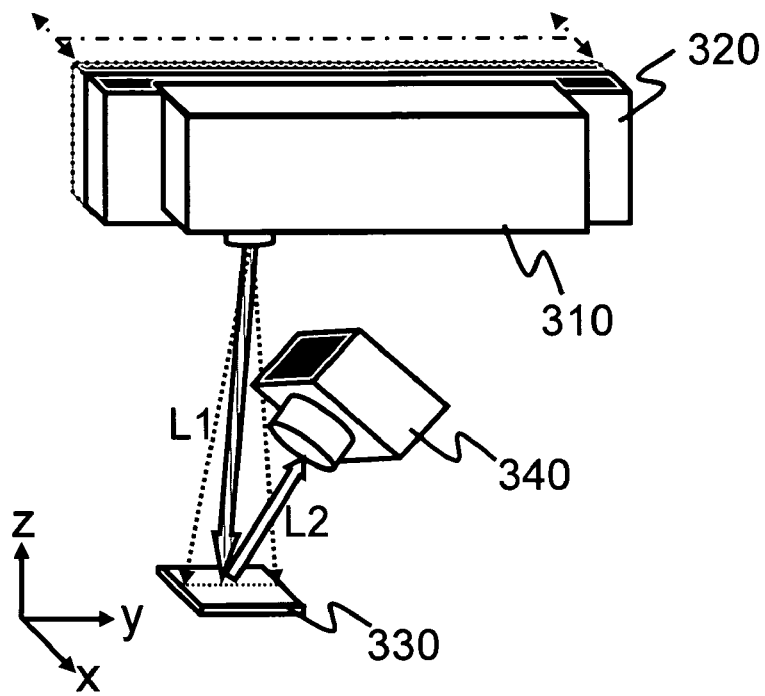
FIG. 3A is a constructional view of an optical detection apparatus according to a first embodiment of the invention.

As shown in FIG. 3A, an optical detection apparatus according to a first embodiment of the invention is illustrated. In this case, a light module 310 generates excitation light L1 scanning in Y-axis, and the light module 310 is carried by a carrier 320 to move in a direction nonparallel to Y-axis, so as to achieve two-dimensional scanning. The preferred direction is along X-axis. In other words, the excitation light L1 scanning in Y-axis and moving along X-axis is combined to produce a two-dimensional testing zone in which a labeled sample 330 is placed. The labeled sample 330 excited by the linear scanning light to emit emission light L2. A light receiver 340 receives the emission light L2 and processes to form image signals of the labeled sample 330.

In this case, the labeled sample is a test sample labeled with or having fluorescent compounds, or colorimetric compounds. The fluorescent compounds may be fluorescent groups, quantum dot particles, other dye particles or an antibody conjugated with indocarbocyanine dyes or fluorescent proteins, etc., such as fluorescein, rhodamine, dichlorofluorescein, hexachlorofluorescein, tetramethylrhodamine, indocarbocyanine dyes, Texas Red, ethidium bromide, chelated lanthanides, phycoerythrin, GFP, avidin fluorescein (FITC), IgG- phycoerythrin (PE), anti-fluorescein (FITC), IgG2a PE-Cy5, TRITC (tetramethylrhodamine-5-isothiocyanate), and the like. The indocarbocyanine dyes may be Cy3, Cy5, Cy5.5, or Cy7, etc. The fluorescent proteins may be R-PE, or B-PE, etc. The colorimetric compounds may be colorimetric enzymes such as alkaline phosphatase (AP) or horseradish peroxidase (HRP).

Figure 3B:
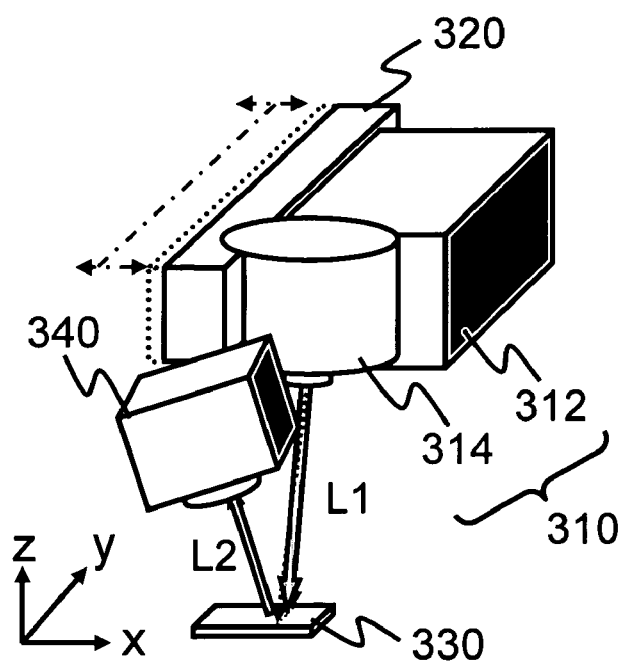
FIG. 3B is a constructional view of an optical detection apparatus according to a second embodiment of the invention.

The light module 310 includes a laser module 312 and a scan module 314. The laser module 312 provides excitation light L1 to the scan module 314. The scan module 314 continuously reflects and introduces the excitation light L1, and provides a linear scanning light in Y-axis by changing of the reflection angle. The carrier 320 moves the light module 310 in a direction nonparallel to Y-axis, such as along X-axis, so as to achieve two-dimensional scanning as shown in FIG. 3B.

Figure 3C:
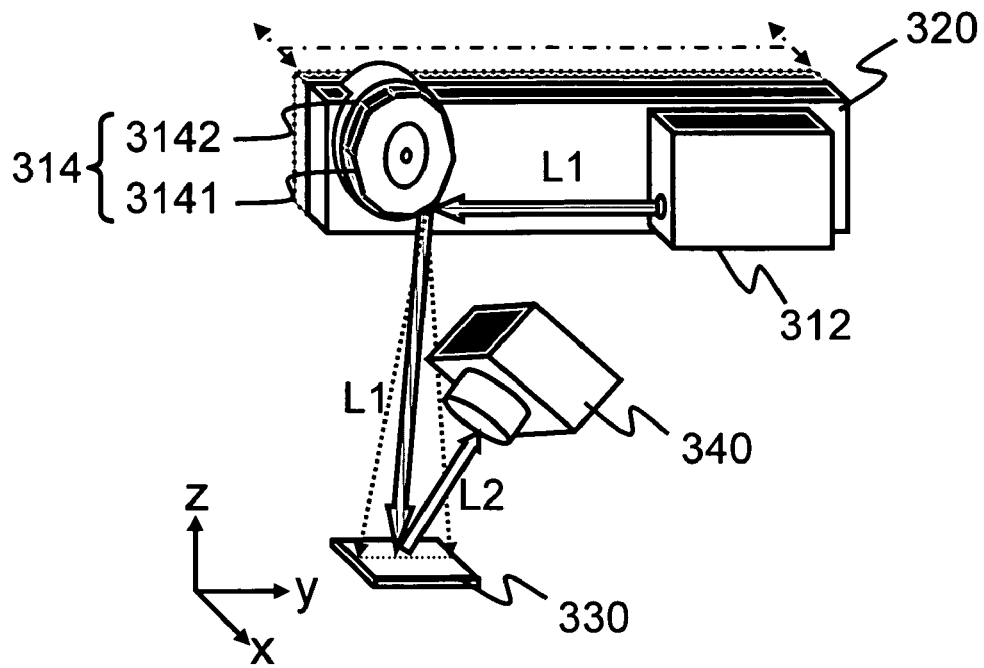
FIG. 3C is a constructional view of an optical detection apparatus according to a third embodiment of the invention.

The scan module 314 includes a polygonal mirror 3141 and a motor 3142 as shown in FIG. 3C. Moreover, the polygonal mirror 3141 includes a polyhedron rotor having poly reflective surfaces, or is formed with mirrors. The polyhedron rotor having poly reflective surfaces may be made of a polyhedron rotor and scanning mirrors embedded thereon. The scan module 314 receives the excitation light L1, and continuously reflects and introduces the excitation light L1 to provide a linear scanning light in Y-axis by rotating the polygonal mirror 3141, which is formed that the poly reflective surfaces or poly-mirrors arrange on the polyhedron rotor. As each reflective surface or mirrors rotates and passes through the excitation light L1, it reflects and introduces the excitation light L1 to form a Y-axis scanning light that makes up one part of the continuous one-dimensional scanning light. In other words, the polygonal mirror 3141 rotated by the motor 3142 continuously reflects and introduces the excitation light L1 into a Y-axis scanning light caused by each reflective surface or mirrors which arrange on the polyhedron rotor rotated by the motor.

Figure 3D:
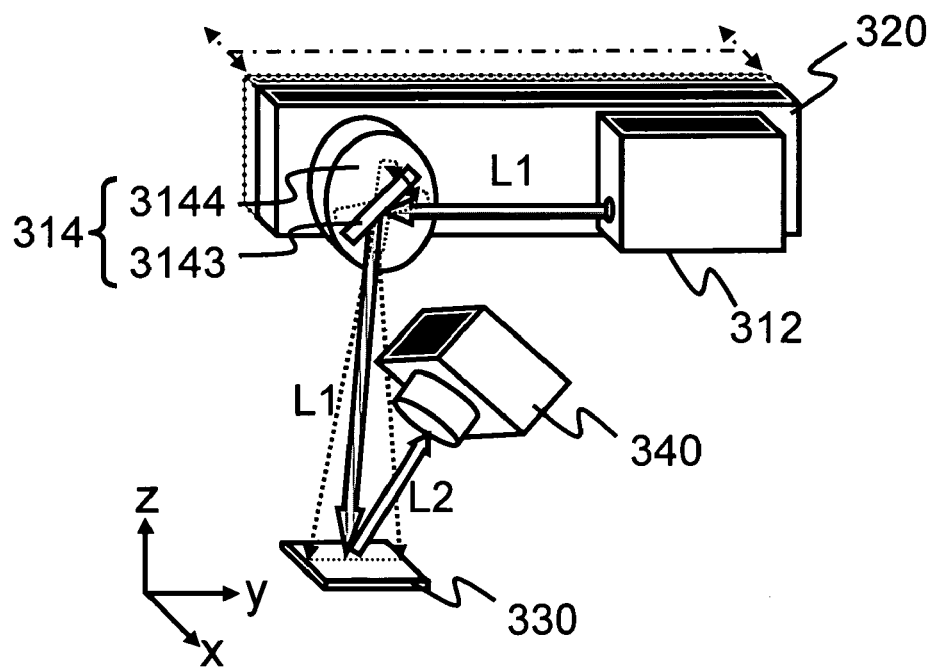
FIG. 3D is a constructional view of an optical detection apparatus according to a fourth embodiment of the invention.
Figure 3E:
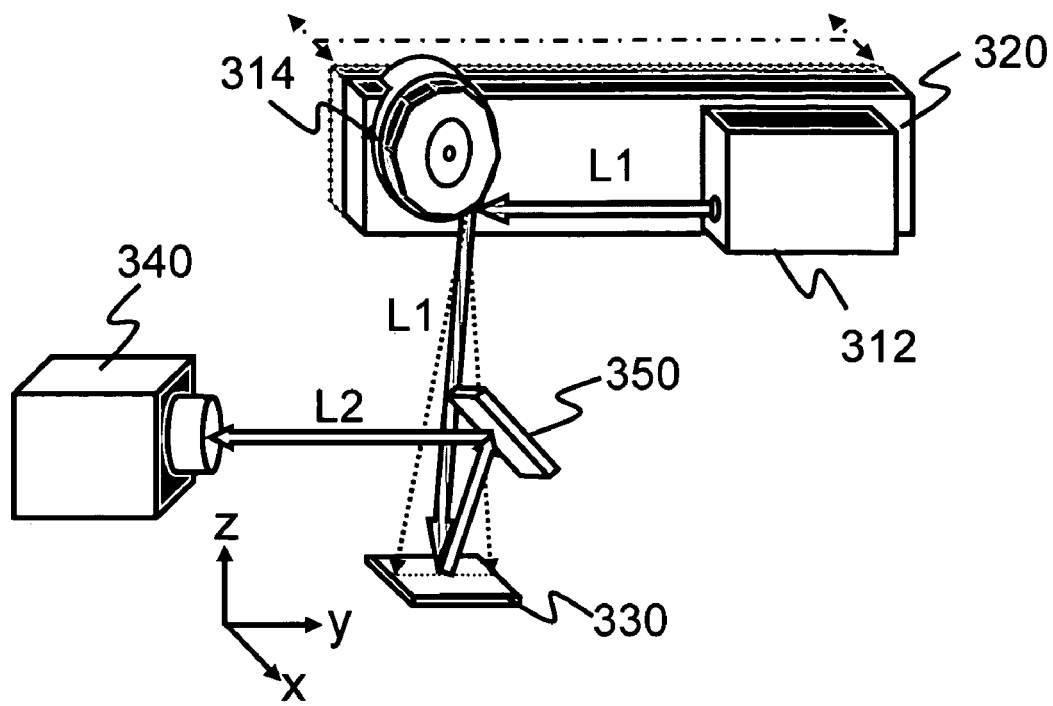
FIG. 3E is a constructional view of an optical detection apparatus according to a fifth embodiment of the invention.
Figure 3F:
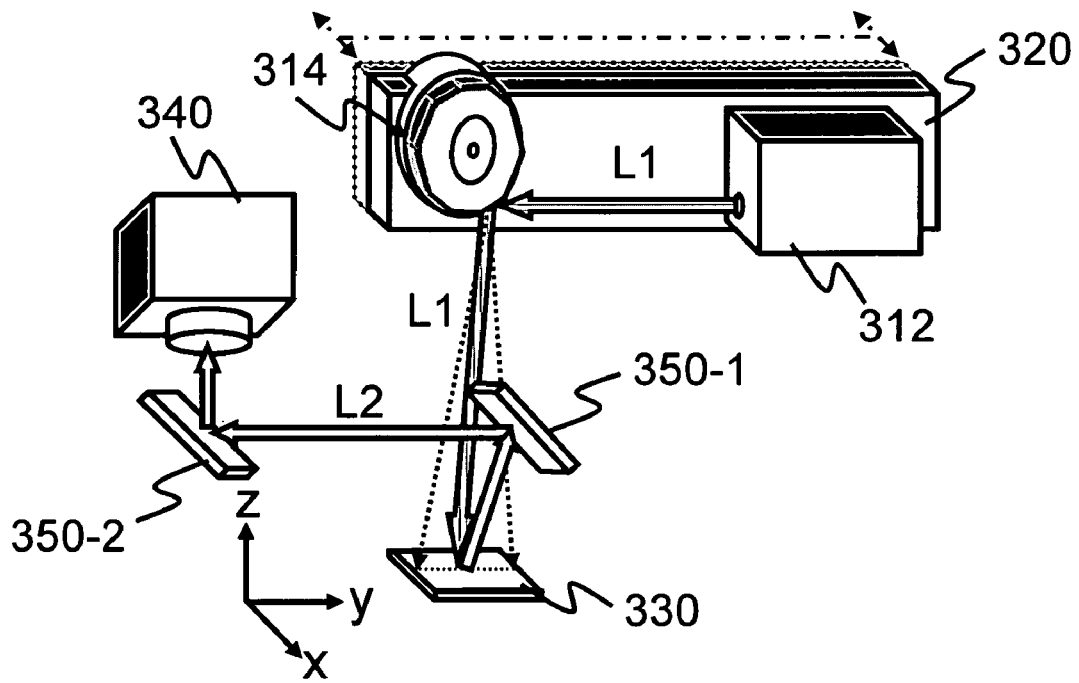
FIG. 3F is a constructional view of an optical detection apparatus according to a sixth embodiment of the invention.
Figure 3G:
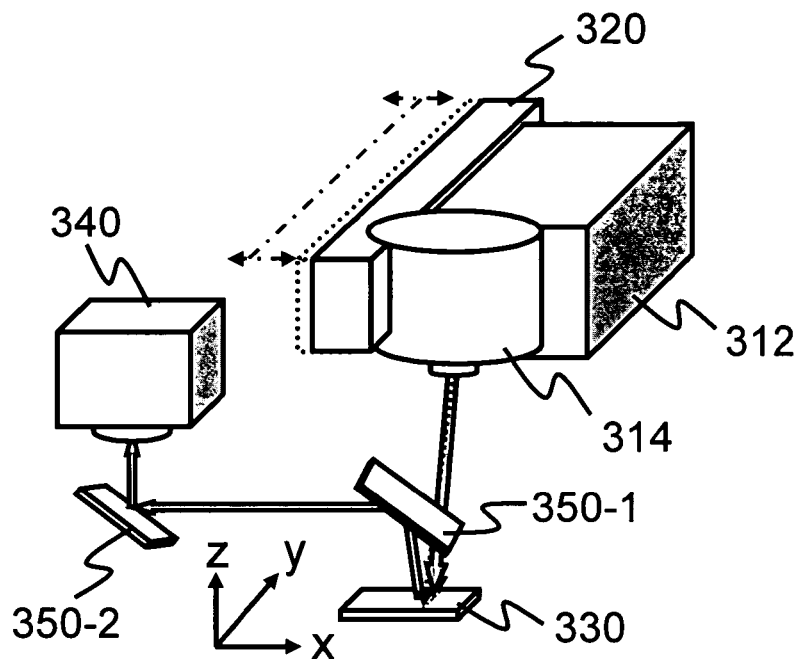
FIG. 3G is a side view of an optical detection apparatus according to a fifth embodiment of the invention.

With reference to FIG. 3D, the scan module 314 is as a galvanometer as disclosed in U.S. Pat. Nos. 6,630,063 and 6,819,468. The laser module 312 generates excitation light L1 passing through the galvanometer and formed into Y-axis scanning light.

The galvanometer comprises a reflective mirror 3143 and a driving unit 3144. The reflective mirror 3143 has one reflective surface. The driving unit 3144 drives the reflective mirror 3143 so that the reflective mirror 3143 oscillates and simultaneously reflects the excitation light L1 to form a Y-axis scanning light that makes up one of the continuous one-dimensional scanning light.

The emission light L2 emitted by the labeled sample 330 can be guided by at least a mirror 350 (or mirrors 350-1, 350-2) to the light receiver 340. The mirror 350 or mirrors 350-1, 350-2 guide the emission light L2 to any suitable position in the apparatus where the light receiver 340 locates so as to compact the apparatus to a smaller size as shown in FIGS. 3E to 3H. The excitation light L1 is reflected by the scan module 314 and passed to the testing zone in a tilt angle, so that the excitation light L1 passes aside the mirror 350 or mirrors 350-1.

The laser module 312 can be a laser generator to generate excitation light L1 and pass the light directly to the scan module 314 without turning. Then, the scan module 314 reflects the excitation light L1 to the testing zone for Y-axis scanning. In other words, the laser module can be a larger size laser generator to generate the direct light path to the scan module, thereby further compact the apparatus.

Figure 3H:
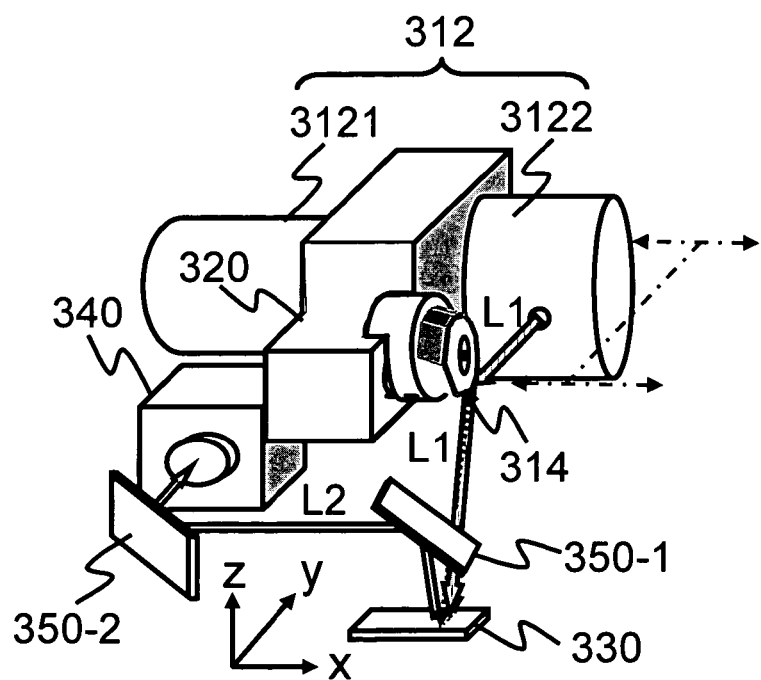
FIG. 3H is a constructional view of an optical detection apparatus according to a seventh embodiment of the invention.

As shown in FIG. 3H, the laser module 312 can be a laser generator 3121 connected with a collimation and coupling lenses 3122. The laser generator 3121 generates excitation light L1 passing via the collimation and coupling lenses 3122 to the scan module 314. Then, the scan module 314 reflects the excitation light L1 to the testing zone for Y-axis scanning. The laser generator 3121 can be a tubular laser.

The laser module 312 may have an array of laser generators, which generate the laser beams with different wavelengths, respectively, and a collimation and coupling lenses to couple the laser beams into the excitation light. Besides, the laser module 312 may be an array of the same laser generators for providing the linear scanning light, and the laser generators may be laser diodes. Further, a collimation and coupling lens is used to collimate the scanning light to the testing zone.

Figure 3I:
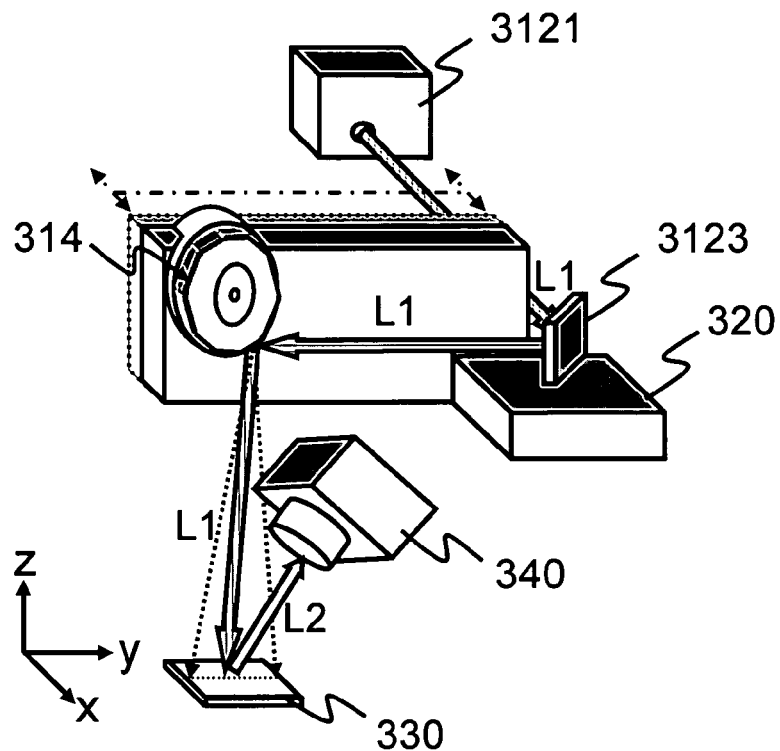
FIG. 3I is a constructional view of an optical detection apparatus according to an eighth embodiment of the invention.
Figure 3J:
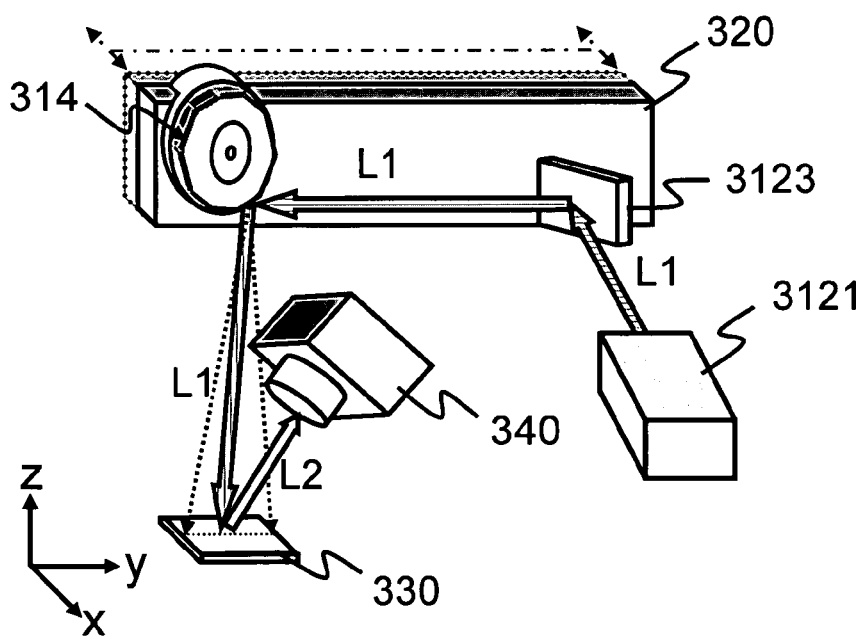
FIG. 3J is a constructional view of an optical detection apparatus according to an ninth embodiment of the invention.

Furthermore, the laser generator(s) cannot be installed on the carrier, that is, the laser module(s) is/are steadfastly installed. It assumed that the laser module includes a laser generator for generating the excitation light. In this case, the laser generator 3121 is steadfastly installed, and the laser module further includes a mirror 3123 which is installed on the carrier 320 to move with the scan module 314 and to reflect the excitation light L1 to the scan module 314, as shown in FIGS. 3I and 3J. Moreover, the excitation light generated by the laser generator(s) can be collimated and guided by the collimation and coupling lenses (not shown in FIGS. 3I and 3J) first, and then be reflected by the mirror.

Figure 3K:
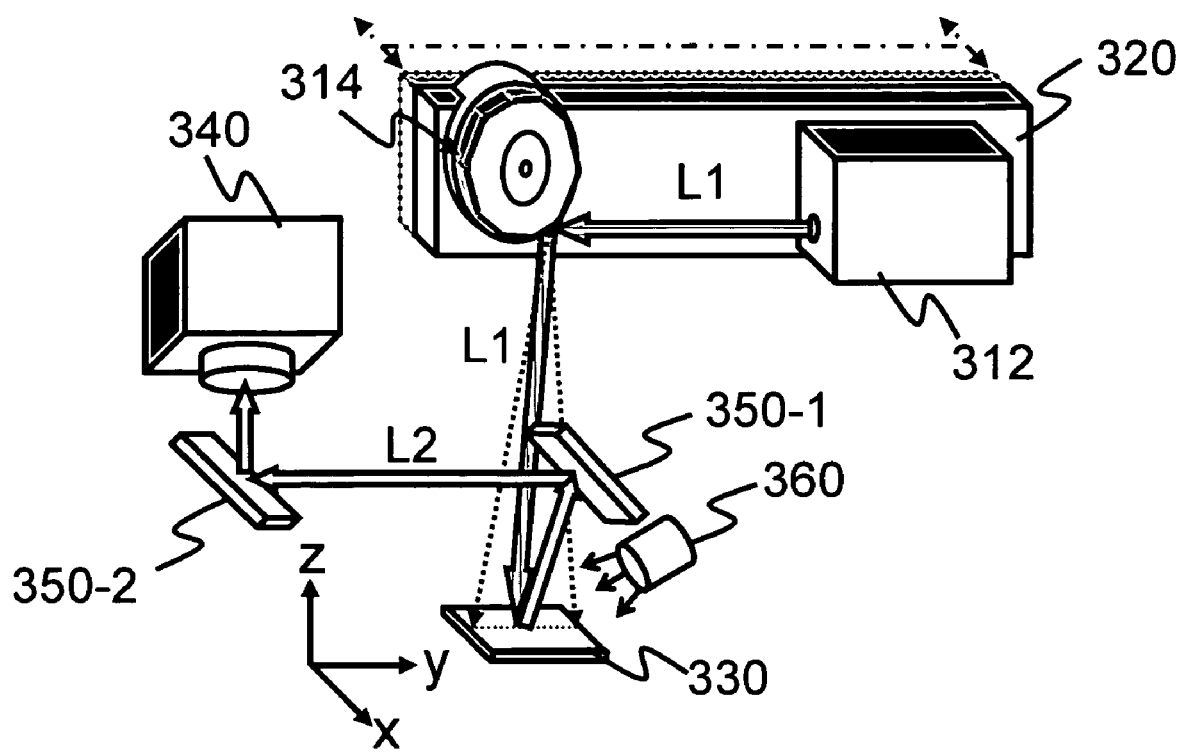
FIG. 3K is a constructional view of an optical detection apparatus according to an tenth embodiment of the invention.

As shown in FIG. 3K, a light generator 360 is mounted upon the testing zone to provide illumination to the labeled sample so that the apparatus can also be used for detecting the colorimetric image of the labeled sample. The light generator 360 has light-emitting diodes suitably arranged for even illumination through studies of optical simulation. In other words, the labeled sample with colorimetric compounds, such as colorimetric enzymes, is illuminated by the light generator 360, so as to enable the light receiver 340 to form the colorimetric image according to the light from the labeled sample. In this case, the light generator may be a light emitting diode (LED).

The carrier 320 includes an actuator for providing nonparallel to Y-axis scanning movement of the excitation light L1. Moreover, the preferred scanning movement is X-axis scanning movement. The actuator can be a stepping motor, gear AC/DC motor, linear motor, a screw or a ballscrew system, but is not limited to these devices.

The light receiver 340 includes an image lens, a filter and an image-sensing module. The image lens receives the emission light L2, passes it through the filter to get a certain wavelength light for the image-sensing module to form image signals of the labeled sample corresponding to the emission light. The filter can be mechanically replaced according to characteristics of the fluorescence image. The image-sensing module can be a charge-coupled device (CCD). A cooling element can be applied to reduce the dark current of the CCD and increase the signal-to-noise ratio.

Therefore, the optical detection apparatus of the invention has both functions of detection for the image signals by fluorescence labelling and colorimetric. That is, the laser module may be used for detecting the fluorescence image and a portion of the colorimetric images, and the light generator, such as the LED, may be used for detecting another portion of the colorimetric images. Further, the light receiver is used for receiving the emission light from the labeled sample in both above detection modes.

The invention further includes a detecting method comprising the following steps. First, provide linear excitation light with a tilt angle. Then, move the linear excitation light in a direction perpendicular to the linear direction of the linear excitation light to form a testing zone. Further, illuminate and excite a labeled sample in the testing zone to get an emission light. And, receive the emission light and form the image signals of the labeled sample corresponding to the emission light to acquire an image. That is, the tilt angle means that the light path of the linear excitation light and that of the emission light are different from each other.

In the step of providing linear excitation light with a tilt angle, there are steps of generating excitation light and forming scanning lines by continuously reflecting the excitation light with change of reflection angle of a scan module. The excitation light can be directly passed to the scan module, or collimated by a collimator before being passed to the scan module.

There is at least a mirror to reflect the emission light to a light receiver.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An optical detection apparatus for detecting image signals of a labeled sample, comprises:

at least a laser generator for providing an excitation light and transmitting the excitation light; and a scan module for continuously reflecting the excitation light and introducing the excitation light to provide a linear scanning light by changing a reflection angle;

a carrier for carrying the laser generator and the scan module, so that the laser generator and the scan module move together in a direction nonparallel to a linear direction of the linear scanning light so as to provide a two-dimensional testing zone in which the labeled sample is placed and is excited by the linear scanning light to emit an emission light; and a light receiver for receiving the emission light and forming the image signals of the labeled sample according to the emission light.

2. The optical detection apparatus of claim 1, wherein the scan module comprises:
   a polygon mirror for reflecting the excitation light; and
   a motor for rotating the polygon mirror to changing the reflection angle of the polygon mirror so that the excitation light is reflected into scanning light.

3. The optical detection apparatus of claim 2, wherein the polygon mirror comprises a polyhedron rotor and a plurality of scanning mirrors respectively embedded on a plurality of surfaces of the polyhedron rotor.

4. The optical detection apparatus of claim 2, wherein the polygon mirror is formed with a plurality of mirrors.

5. The optical detection apparatus of claim 1, wherein the scan module is a galvanometer which comprises a reflective mirror having one reflective surface and a driving unit driving the reflective mirror so that the reflective mirror oscillates and simultaneously reflects the excitation light to form a scanning light.

6. The optical detection apparatus of claim 1, further comprising:
   a mirror, which is carried by the carrier to move with the scan module, for reflecting the excitation light to the scan module.

7. The optical detection apparatus of claim 1, further comprising:
   a collimation and coupling lenses connected to the laser generator for collimating and guiding the excitation light so as to transmit to the scan module.

8. The optical detection apparatus of claim 1, further comprising:
   a collimation and coupling lenses connected to the laser generator for collimating and guiding the excitation light; and
   a mirror, which is carried by the carrier to move with the scan module, for reflecting the excitation light from the collimation and coupling lenses to the scan module.

9. The optical detection apparatus of claim 1, further comprises:
   at least a mirror for guiding the emission light from the labeled sample to the light receiver, wherein the testing zone, the mirror and the light receiver are serially arranged in an emission light path.

10. The optical detection apparatus of claim 9, wherein the excitation light passes aside the mirror.

11. The optical detection apparatus of claim 1, further comprises:
    a light generator for providing an illumination to the labeled sample.

12. The optical detection apparatus of claim 11, wherein the light generator has a plurality of light-emitting diodes.

13. The optical detection apparatus of claim 1, wherein the preferred direction, in which the carrier moves, is perpendicular to the linear direction of the linear scanning light.

14. The optical detection apparatus of claim 1, wherein the carrier comprises an actuator for generating scanning motion.

15. The optical detection apparatus of claim 1, wherein the light receiver comprises:
    an image lens for receiving the emission light from the labeled sample;
    a filter for getting a certain wavelength emission light; and
    an image-sensing module for forming image signals of the labeled sample corresponding to the filtered emission light.

16. The optical detection apparatus of claim 15, wherein the image-sensing module is a charge-coupled device (CCD).

* * * * *